US008507868B2

(12) United States Patent
Maucec

(10) Patent No.: US 8,507,868 B2
(45) Date of Patent: Aug. 13, 2013

(54) SYSTEMS AND METHODS FOR DETERMINING FLUID MOBILITY IN ROCK SAMPLES

(75) Inventor: Marko Maucec, Englewood, CO (US)

(73) Assignee: Landmark Graphics Corporation, Houston, TX (US)

( * ) Notice: Subject to any disclaimer, the term of this patent is extended or adjusted under 35 U.S.C. 154(b) by 207 days.

(21) Appl. No.: 13/040,396

(22) Filed: Mar. 4, 2011

(65) Prior Publication Data

US 2012/0223235 A1  Sep. 6, 2012

(51) Int. Cl.
G01T 1/164 (2006.01)
G01T 1/20 (2006.01)
G01T 1/166 (2006.01)

(52) U.S. Cl.
USPC ............... 250/363.03; 250/362; 250/363.04

(58) Field of Classification Search
USPC ............. 250/362, 363.03, 259, 260, 253
See application file for complete search history.

(56) References Cited

U.S. PATENT DOCUMENTS

| | | | | |
|---|---|---|---|---|
| 2,755,660 | A | * | 7/1956 | Kammermeyer et al. ......... 73/38 |
| 4,555,934 | A | * | 12/1985 | Freeman et al. ................. 73/38 |
| 4,782,899 | A | * | 11/1988 | Richardson ................ 166/252.2 |
| 5,164,590 | A | | 11/1992 | Coles et al. |
| 5,498,960 | A | * | 3/1996 | Vinegar et al. ................. 324/303 |
| 5,679,885 | A | * | 10/1997 | Lenormand et al. .............. 73/38 |
| 5,753,919 | A | * | 5/1998 | Prain et al. ..................... 250/368 |
| 6,220,371 | B1 | | 4/2001 | Sharma et al. |
| 7,408,546 | B2 | | 8/2008 | Serra |
| 7,734,331 | B2 | * | 6/2010 | Dhawale et al. ............... 600/431 |
| 7,767,958 | B2 | | 8/2010 | Luling et al. |
| 2008/0230703 | A1 | * | 9/2008 | Kadrmas et al. ......... 250/363.03 |
| 2009/0092549 | A1 | * | 4/2009 | Kihlberg et al. ............. 424/1.81 |
| 2010/0057819 | A1 | | 3/2010 | Panin |
| 2010/0135536 | A1 | | 6/2010 | Dvorkin et al. |
| 2010/0151456 | A1 | | 6/2010 | Ataman et al. |
| 2010/0284247 | A1 | * | 11/2010 | Manning et al. ................. 367/28 |
| 2010/0316275 | A1 | * | 12/2010 | Stolin et al. .................... 382/131 |

FOREIGN PATENT DOCUMENTS

EP 1466955 A 10/2004
EP 1967869 A1 9/2008

OTHER PUBLICATIONS

K. H. Hellmuth et al., "Imaging and analyzing rock porosity by autoradiography and Hg-porosimetry/X-ray computertomography—applications", Phys. Chem. Earth (A), vol. 24, No. 7, pp. 569-573, 1999.*
J.P.K. Seville et al., "Positron emission imaging in chemical engineering", Advances in Chemical Engineering, vol. 37, pp. 149-178, 2009.*
Michael Richter et al., "Positron emission tomography for modelling of geochemical transport processes in clay", Radiochim Acta, vol. 93, pp. 643-651, 2005.*

(Continued)

Primary Examiner — David Porta
Assistant Examiner — Abra Fein
(74) Attorney, Agent, or Firm — Crain Caton & James; Bradley A. Misley

(57) ABSTRACT

Systems and methods for determining fluid mobility in rock samples using time-lapse position emission particle tracking (PEPT). The systems and methods use PEPT to determine permeability in rock samples, such as shale, that have a permeability of less than one micro-darcy by recording gamma-ray emissions from a tag using a positron emission tomography camera as the tag traverses with a fluid through the pores in the rock sample.

30 Claims, 3 Drawing Sheets

(56) References Cited

OTHER PUBLICATIONS

R.P. Maguire et al., "Positron emission tomography of large rock samples using a multiring PET instrument", IEEE Transactions on Nuclear Science, vol. 44, No. 1, pp. 26-30, 1997.*
C. Degueldre et al., "Porosity and pathway determination in crystalline rock by positron emission tomography and neutron radiography", Earth and Planetary Science Letters, vol. 140, pp. 213-225, 1996.*
Arthur M. Horton, Jr. and Danny Wedding, "The Neuropsychology Handbook: Third Edition", Springer Publishing Company, LLC., New York, 2008.*
Hiroshi Watabe et al., "Performance of list mode data acquisition with ECAT EXACT HR and ECAT EXACT HR+ positron emission scanners", Annals of Nuclear Medicine, vol. 20, No. 3, pp. 189-194, 2006.*
Hawkesworth, M.R., Fowles, P., Crilly, J.F., Jefferies, N.L. & Jonkers, G.;Nonmedical Applications of a Positron Camera; Nuclear Instruments and Methods in Physics Research A310; 1991; pp. 423-434; North Holland.
Degueldre, C., Pleinert, H., Maguire, P., Lehman, E., Missimer, J., Hammer, J., Leenders, K., Bock, H. & Townsend, D.; Porosity and Pathway Determination in Crystalline Rock by Positron Emission Tomography and Neutron Radiography; Earth and Planetary Science Letters, 140, 1-4; 1996; pp. 213-225.
Maguire, R.P., Missimer, J.H., Emert, F., Townsend, D.W., Dollinger, H. & Leenders, K.L. ; Positron Emission Tomography of Large Rock Samples Using a Multiring PET Instrument; IEEE Transactions of Nuclear Science, Feb. 1997; pp. 26-30; vol. 44, No. 1.
Spinks, T.J., Jones, T., Bloomfield, P.M., Bailey, D.L., Miller, M., Hogg, D., Jones, W.F., Vaigneur, K., Reed, J., Young, J., Newport, D., Moyers, C., Casey, M.E. & Nutt, R.; Physical Characteristics of the ECAT EXACT3D Positron Tomograph; Phys. Med. Biol. 45; 2000; pp. 2601-2618;IOP Publishing Limited; United Kingdom.
Elangovan, Vidya & Whitaker, Ross T.; From Sinograms to Surfaces; A Direct Approach to the Segmentation of Tomographic Data; International Conference on Medical Image Computing and Computer-Assisted Intervention (MICCAI); Oct. 2001; pp. 213-223; Utrechct, The Netherlands.
Caselles, Vicent, Kimmel, Ron & Sapiro, Guillermo; Geodesic Active Contours; International Conference on Computer Vision, IEEE Computer, Society Press; 1995; pp. 694-699.
Lu, Weiguo & Mackie, Thomas R.; Tomographic Motion Detection and Correction Directly in Sinogram Space; Physics in Medicine and Biology, 47; 2002; pp. 1267-1284;IOP Publishing Ltd.; United Kingdom.
Malladi, Ravikanth, Sethian, James A. & Vemuri, Baba C.; Shape Modeling with Front Propagation; A Level Set Approach; IEEE Transactions on Pattern Analysis and Machine Intelligence; Feb. 1995; pp. 158-175; vol. 17, No. 2.
Jaffe, Amy Myers; Shale Gas Will Rock The World; The Wall Street Journal; May 10, 2010; 5 pgs.
Staas, Peter; The Future of Shale Gas is International; Jul. 11, 2010; 3 pgs.
Wylie, Glenda, Eberhard, M. & Mullen, Mike; Trends in Unconventional Gas; Oil and Gas Journal; Dec. 17, 2007; 20 pgs.
Soliman, M.Y.; Technique for Considering Fluid Compressibility and Temperature Changes in Mini-Frac Analysis; SPE15370; Oct. 5-8, 1986; 11pgs.; 61st SPE ATCE: New Orleans, Louisiana.
Soliman, M.Y., Kuhlman, R.D. & Poulsen, D.K.; Minifrac Analysis for Heterogeneous Reservoirs; Paper No. CIM/SPE 90-5; Jun. 10-13, 1990; pp. 5-1-5-9; Petroleum Society of CIM/Society of Petroleum Engineers; Calgary, Canada.
Edwards, W.J., Gauthier, S. & Clarkson, B.; New Frac-Pack Redesign Methodology Improves Estimation of Tip screenout Post-FET; SPE98171; Feb. 15-17, 2006 ; pp. 216-222; SPE International Symposium and Exhibition on Formation Damage Control; Lafayette, Louisiana.
Smith, Jeff, Vitthal, Sanjay; McGowen, James M. & Dusterhoft, Ron; How Minifracs Alter Leakoff and Ways to Counteract It; SPE58767; Feb. 23-24, 2000; pp. 1-15; SPE International Symposium and Exhibition on Formation Damage Control; Lafayette, Louisiana.
Dyer, George, Gani, Setiawan Rudy & Gauntt, Gary; Innovative Perforating Techniques Show Promising Results in Problematic Deep Depleted Gas Sands; IADC/SPE47807; Sep. 7-9, 1988; pp. 1-7; IADC/SPE Asia Pacific Drilling Conference; Jakarta, Indonesia.
Waltman, Bart, Foo, Fong-Fong (Allison) and Strobel, Marshal; Streamlining the Frac Pack Process; Oilfield Technology; Oct. 2009; 20 pgs.
Dusterhoft, Ron, Nguyen, Philip & Conway, Mike; Maximizing Effective Proppant Permeability Under High-Stress, High Gas-Rate Conditions; SPE90398; Sep. 26-29, 2004; pp. 1-16; SPE Annual Technical Conference; Houston, Texas.
Buller, Dan; Magnetic Resonance Application in Gas Shales; SPWLA Presentation; Southwest Technology Principle Petrophysical; May 14-18, 2011; 8 pgs.; 2011 SPWLA Symposium.
Volkwyn, T.S.; Buffler, A.; Govender, I.; Franzidis, J.P.; Morrison, A.J.; Odo, A.; Van Der Meulen, N.P. & Vermeulen, C.; Studies of the Effect of Tracer Activity on Time-Averaged Position Emission Particle Tracking Measurements on Tumbling Mills at PEPT Cape Town; Minerals Engineering 24; 2011; pp. 261-266; Elsevier.
Swindell, W. & Webb, Steve; The Physics of Medical Imaging (X-Ray Transmission Computer Tomography); Medical Science Series, Chapter 4; 1988; pp. 98-127; Taylor & Francis; New York.
Buffler, A., Govender, I., Cilliers, J.J., Parker, D.J.; Franzidis, J.P., Mainza, A., Newman, R.T., Powell, M. & Van Der Westhuizen, A.; PEPT Cape Town: A New Position Emission Particle Tracking Facility at iThemba LABS; Proceedings of International Topical Meeting on Nuclear Research Applications and Utilization of Accelerators; May 4-8, 2009; pp. 1-8; AP/IE-5; IAEA; Vienna.
Saha, Gopel B.; 3-Data Acquisition and Corrections (PET Data Acquisition); Basics of PET Imaging: Physics, Chemistry and Regulations; 2010; pp. 41-45; 2nd Edition; Springer Science and Business Media LLC; New York, New York.
Rotary Sidewall Coring (RSCT™) Tool (Halliburton); Sep. 15, 2010; 1 pg.
Hostile Rotary Sidewall Coring (RSCT™) Tool (Halliburton); Sep. 15, 2010; 1 pg.
Shale (3D Imaging & Computing of Advanced Rock Properties); May 24, 2010; 1 pg.
Norman, W.D.; Pourciau,R.D.; Dusterhoft, R. & Schubarth, S.; Understanding the Effects of Reservoir Changes in Sand-Control Completion Performance; SPE 96307; 2005 SPE Annual Technical Conference and Exhibition; Dallas, TX; Oct. 9-12, 2005; 10 pgs.
Lee W. Young, Notification of transmittal of the international search report and the written opinion of the international searching authority, International Application No, PCT/US12/27749, Jul. 16, 2012, 9 pages, International Searching Authority, Alexandria, Virginia, USA.
S.R. Ogilvie et al, The influence of deformation bands upon fluid flowing using profile permeametry and positron emission tomography, Geophysical Research Letters, Jan. 1, 2001, 4 pages, vol. 28, No. 1, Department of Geology and Petroleum Geology, University of Aberdeen, Aberdeen, Scotland.
R.R. Ryan et al, Chemistry—Nuclear Chemistry Division Oct. 1980-Sep. 1981, LA-9381-PR Progress Report, May 1982, 176 pages, UC-4, Los Alamos National Laboratory, Los Alamos, New Mexico.

* cited by examiner

SYSTEMS AND METHODS FOR DETERMINING FLUID MOBILITY IN ROCK SAMPLES

CROSS-REFERENCE TO RELATED APPLICATIONS

Not applicable.

STATEMENT REGARDING FEDERALLY SPONSORED RESEARCH

Not applicable.

FIELD OF THE INVENTION

The present invention relates to systems and methods for determining fluid mobility in rock samples. More particularly, the present invention relates to systems and methods for determining fluid mobility in rock samples using time-lapse positron emission particle tracking ("PEPT").

BACKGROUND OF THE INVENTION

One of the biggest challenges to determining fluid mobility in rock samples is the very fine microstructure in some rock samples—like shale. Shale significantly differs from all other formation rocks in the grain size, which corresponds to very low values for porosity ($\Phi$) and permeability (k).

Conventional techniques for determining fluid mobility in rock samples include:
Nuclear Magnetic Resonance (NMR);
3D CT scanning, that enables contouring density differences i.e. contrast in the scanned image;
X-ray diffraction; and
SEM evaluation of rock samples.

One of the main disadvantages is that such conventional techniques can only operate with and handle very small rock samples referred to as core plugs, which are not representative of the entire sample—much less the reservoir. In other words, the fluid mobility determined by such conventional techniques is not representative of the in-situ fluid mobility and thus, must be adjusted for a more accurate representation. The determination of fluid mobility by any of the foregoing conventional techniques may be improved by "upscaling," which extrapolates petrophysical properties from the core-plug scale to determine the simulation-grid scale. Many upscaling techniques are well known and available such as, for example, power-law average, renormalization, pressure-solver, tensor and pseudofunction techniques. In short, upscaling replaces a number of heterogeneous fine grid blocks with one equivalent coarse homogeneous grid block. The essence of conventional upscaling requires averaging and extrapolation, which therefore, leads to the loss of information and creates the common problem of blurring the spatially continuous extremes such as, for example, shale barriers and open fractures. Oil and gas recovery mainly depends on the spatial connectivity of the extreme (ultra-low) permeability values, particularly characteristic of small scale shale pores. Determining fluid mobility in rock samples without upscaling is therefore, preferred.

Other conventional techniques for determining fluid mobility in rock samples include: i) grinding the rock samples; ii) removing all of the water content from the rock samples; and iii) injecting He or Hg into the rock samples. These techniques, however, are not optimal because they skew the original geo-mechanical properties of the rock sample before determining fluid mobility and may still require upscaling for very small rock samples (core plugs).

As a result, applications of positron radiation detection have emerged from more traditional medical imaging applications using Positron Emission Tomography ("PET"). In standard PET imaging, data acquired in two-dimensional (2D) or three-dimensional (3D) form are stored in sinograms that consist of rows and columns representing angular and radial samplings, respectively. The raw data are pre-binned by the hardware into the sinogram format. Due to the pre-binning operation, the data in the sinogram format result in lower resolution from the original raw data, which results in the loss of valuable information about the scanned object. In sinogram format, the acquired data in each row are compressed (summed) along the depth of the object and must be decompressed to provide information along this direction. In *Non-medical Applications of a Positron Camera*, Nuclear Instruments and Methods in Physics Research A310, 1991, pp. 423-434, written by Hawkesworth, et al., for example, PET is used to produce images every ten (10) minutes to track fluid flow in rock samples. This technology, however, is limited because the acquired data is stored in sinograms, which require more time to process than the original raw data stored in list mode. As a result, the image rate is slow (1 every 10 minutes), which lowers the image resolution.

In *Porosity and Pathway Determination in Crystalline Rock by Positron Emission Tomography and Neutron Radiography*, Earth and Planetary Science Letters 140, 1996, pp. 213-225, written by Degueldre, et al., the fluid pathway and porosity in crystalline rock samples have been studied with a high-resolution PET camera. The results demonstrate original water carrier features in granodiorite pieces 20 cm in size and in simulated features with porosities on the order of 20%. In *Positron Emission Tomography of Large Rock Samples Using a Multiring PET Instrument*, IEEE Transactions on Nuclear Science, Vol. 44, No. 1, 1997, pp. 26-30, written by Maguire, et al., the use of PET has been extended to a multi-ring PET camera and demonstrates that the measurements of porosity in large rock samples (21.5 cm) are indeed practicable using 3D acquisition techniques. These techniques, however, are limited to images of just the rock sample structure and therefore, do not illustrate dynamic fluid mobility within the rock sample structure. These techniques also suffer the same shortcomings as other techniques that store acquired data in the sinogram format.

Present research by the University of Cape Town in South Africa utilizes time-lapse PEPT, tags sub-20 µm rock particles and liquids with tags (tracers) having activities of ~100 µCi to determine the mobility of a rock particle in a slurry and a liquid in a column of glass beads. Here, the activity of the tag refers to the radioactive decay in which an unstable (i.e. (radio)active) atomic nucleus looses energy by emitting one or more ionizing particles (i.e. ionizing energy). In PEPT applications, the (radio)active tag emits positrons. Because the acquired data is stored in list mode, the images may be produced at a rate of more than one image per second. As a result, fluid mobility may be determined more accurately because the image quality is improved. This research, however, has not been applied to determine fluid mobility in rock samples, particularly rock samples with small scale pores (less than µD) like shale, because the tag used for the particles is too large for accurate determination of fluid (gas and liquid) mobility.

SUMMARY OF THE INVENTION

The present invention therefore, meets the above needs and overcomes one or more deficiencies in the prior art by providing systems and methods for determining fluid mobility in rock samples using time-lapse position emission particle tracking.

In one embodiment, the present invention includes a method for determining fluid mobility in a rock sample using time-lapse positron emission particle tracking, which comprises the steps of i) selecting a porous rock sample; ii) selecting a fluid for the rock sample; iii) selecting a tag for the fluid; iv) placing the rock sample in a pressurized container; v) introducing the fluid and the tag into pores within the rock sample; vi) recording gamma-ray emissions from the tag using a positron emission tomography camera as the tag traverses with the fluid through the pores in the rock sample placed in the pressurized container; vii) converting the gamma-ray emissions into images at a rate of more than one image every second; and viii) displaying the images.

In another embodiment, the present invention includes a method for determining fluid mobility in a rock sample using time lapse positron emission particle tracking, which comprises the steps of: i) selecting a porous rock sample with a permeability less than one micro-darcy; ii) selecting a fluid for the rock sample that is a gas; iii) selecting a tag for the fluid that is the gas or another gas; iv) placing the rock sample in a pressurized container; v) introducing the fluid and the tag into pores within the rock sample; vi) recording gamma-ray emissions from the tag in a list mode file using a positron emission tomography camera as the tag traverses with the fluid through the pores in the rock sample placed in the pressurized container; vii) converting the gamma-ray emissions into images; and viii) displaying the images.

In step 410, the fluid and the tag are introduced into pores within the rock sample. The fluid and the tag may be introduced into the pores within the rock sample by injecting the fluid and the tag into the pressurized container at one end under a constant pressure and a constant temperature. Alternatively, the fluid and the tag may introduced into the pores within the rock sample by injecting the fluid and the tag directly into the pores within the rock sample before the rock sample is placed in the pressurized container and applying a constant pressure and a constant temperature to the rock sample after it is placed in the pressurized container with the fluid and the tag. The fluid is tagged when it is introduced with the tag into the pores within the rock sample. At this point, the tag is attached to the fluid as the tag traverses with the fluid through the pores within the rock sample and/or the tag travels with the fluid as it traverses with the fluid through the pores within the rock sample. Furthermore, multiple tags may introduced with the fluid into the pores within the rock sample. The fluid and the tag are introduced into the pores within the rock sample at a constant flow rate, a constant pressure and a constant temperature. The flow rate, the constant pressure, the constant temperature, the fluid and the tag may be selected based upon a flow rate, a pressure, and a temperature for a fluid that is indigenous to the rock sample, which represents a target fluid.

BRIEF DESCRIPTION OF THE DRAWINGS

The present invention is described below with references to the accompanying drawings in which like elements are referenced with like referenced numerals, and in which.

DETAILED DESCRIPTION OF THE PREFERRED EMBODIMENTS

The subject matter of the present invention is described with specificity, however, the description itself is not intended to limit the scope of the invention. The subject matter thus, might also be embodied in other ways, to include different steps or combinations of steps similar to the ones described herein, in conjunction with other technologies. Moreover, although the term "step" may be used herein to describe different elements of methods employed, the term should not be interpreted as implying any particular order among or between various steps herein disclosed unless otherwise expressly limited by the description to a particular order. While the following description refers to the oil and gas industry, the systems and methods of the present invention are not limited thereto and may also be applied to other industries to achieve similar results.

Figure 1:
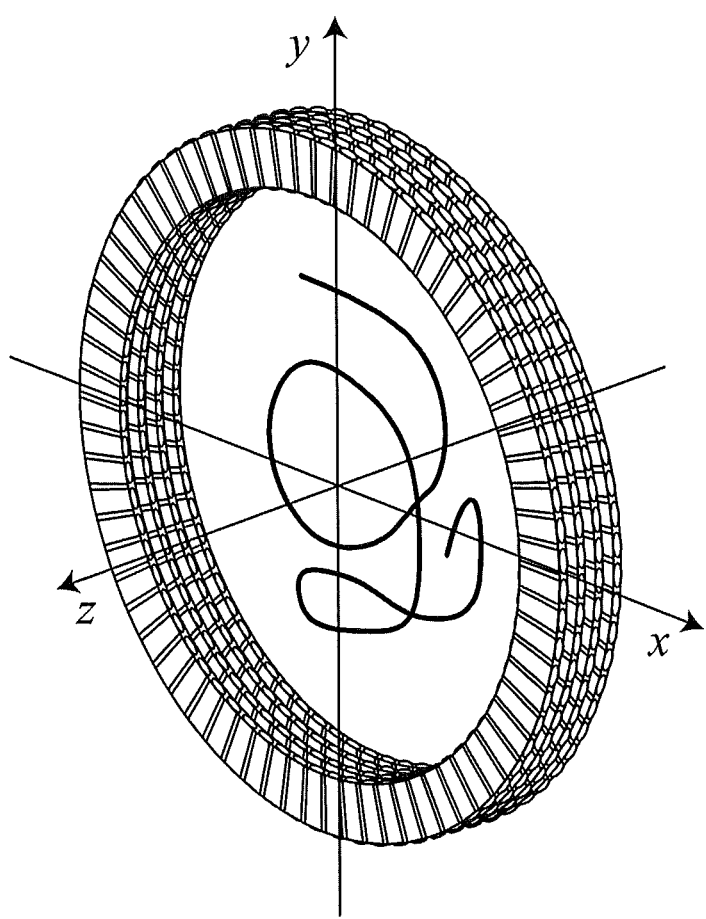
FIG. 1 illustrates PEPT for a single radionuclide tag.

PEPT is basically a technique for measuring the trajectory of one or more tags, which may be used to tag a solid rock particle or a fluid. The tag may be any radioactive nuclide (radionuclide) capable of positron emission. In FIG. 1, for example, the trajectory of a single rock particle tagged with a radionuclide tag is illustrated using PEPT and a PET camera. The radionuclide tag decays through the emission of a positron, which is the antiparticle of an electron. A positron produced in a nuclear decay will rapidly annihilate with an electron, resulting in a pair of 511 keV gamma rays that are emitted almost in opposite directions. If both of these gamma rays are detected at two different points, thereby defining a line of response ("LOR"), then the origin of the gamma ray emissions must have occurred somewhere along the LQR. In other words, the LOR substantially corresponds to a line joining a pair of opposing detectors.

The position of the radionuclide tag can be determined within the field of view of a PET camera using only a small number of measured LOR's. The activity of the tag, however, must be sufficient for enough LOR's to be measured in order to accurately reflect the trajectory of the moving tag. In particular, tags of significantly smaller sizes must be used for PEPT to be reliably accurate for determining fluid mobility in small-scale shale pores. In principle, only two detectors are necessary, however, additional detectors may be used as long as they are paired—meaning positioned opposite one another along a line passing through the center of the PET camera. Because many thousands of gamma-ray emissions can be detected with a PET camera and processed each second, the possibility of determining the position of one or more fast moving radionuclide tags may be realized. Consequently, PEPT may be used to determine fluid mobility in rock samples by tagging a fluid with one or more radionuclide tags.

System Description

The present invention may be implemented through a computer-executable program of instructions, such as program modules, generally referred to as software applications or application programs executed by a computer. The software may include, for example, routines, programs, objects, components, and data structures that perform particular tasks or implement particular abstract data types. The software forms an interface to allow a computer to react according to a source of input. The software may also cooperate with other code segments to initiate a variety of tasks in response to data received in conjunction with the source of the received data. The software may be stored and/or carried on any variety of memory media such as CD-ROM, magnetic disk, bubble memory and semiconductor memory (e.g., various types of RAM or ROM). Furthermore, the software and its results may be transmitted over a variety of carrier media such as optical fiber, metallic wire and/or through any of a variety of networks such as the Internet.

Moreover, those skilled in the art will appreciate that the invention may be practiced with a variety of computer-system configurations, including hand-held devices, multiprocessor systems, microprocessor-based or programmable-consumer electronics, minicomputers, mainframe computers, and the like. Any number of computer-systems and computer networks are acceptable for use with the present invention. The invention may be practiced in distributed-computing environments where tasks are performed by remote-processing devices that are linked through a communications network. In a distributed-computing environment, program modules may be located in both local and remote computer-storage media including memory storage devices. The present invention may therefore, be implemented in connection with various hardware, software or a combination thereof, in a computer system or other processing system.

Figure 2:
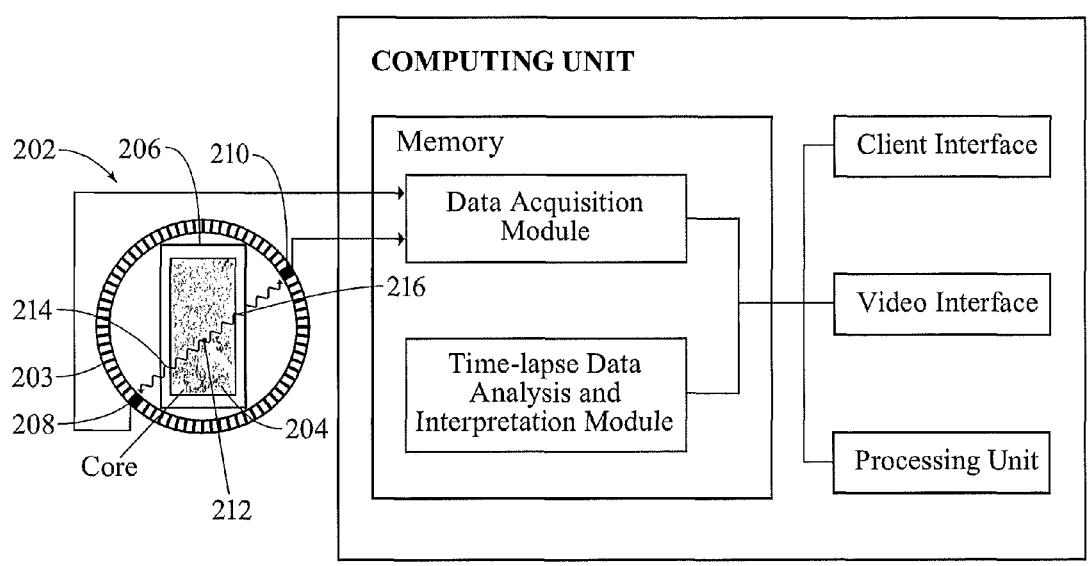
FIG. 2 is a block diagram illustrating one embodiment of a system for implementing the present invention.

Referring now to FIG. 2, a block diagram illustrates one embodiment of a system for implementing the present invention on a computer. The system includes a computing unit, sometimes referred to a computing system, which contains memory, application programs, a client interface, a video interface, a processing unit and a PET camera 202. The computing unit is only one example of a suitable computing environment and is not intended to suggest any limitation as to the scope of use or functionality of the invention.

The PET camera 202 may include any conventional PET camera, such as, for example, the ECAT 'EXACT' 3D model 966 PET camera manufactured by Siemens. The camera 202 has 48 standard bismuth germanate detector elements grouped in blocks of 8×8 forming a detector ring with a diameter of 82 cm and an axial field of view of 23.4 cm. The camera 202 is preferable over other conventional cameras due to its size. The camera 202 is capable of maintaining a sustained data acquisition rate of about 4 million coincidence events per second. The camera 202 also has a superior geometry for studying cylindrical systems in 3D and would allow handling of large rock samples, which represents a tremendous improvement over the standard petrophysical core-plug measurements in rock physics labs. As illustrated in FIG. 2, a shale rock sample 204 about 50 cm in height and about 20 cm in thickness may be positioned in a pressurized container 206. The container 206 is pressurized to simulate pressures and/or temperatures imposed on the rock sample 204 in-situ. Detectors 208, 210 detect emissions generated by pairs of registered incident gamma rays, which are combined in coincidence circuitry within a short time window. In this manner, position information is gained from the detected radiation without the need of a physical collimator (i.e. electronic collimation). For simplicity, the PET camera 202 only illustrates a pair of detectors 208, 210. In practice, all of the detectors in the detector ring 203 are directly wired to the Data Acquisition Module. Alternatively, all of the detectors in the detector ring 203 may be wirelessly connected to the Data Acquisition Module.

Alternatively, the PET camera 202 could be manufactured on a much smaller scale and positioned in a drillstring for deployment downhole in a wellbore. Existing technology, such as the Halliburton RSCT and HRSCT coring tools, could be retrofitted to host a smaller scale PET camera. For example, the RSCT tool drills perpendicularly to the borehole to recover rock samples of $15/16"$ in OD and $1\frac{3}{4}"$ in length. Each rock sample may be withdrawn into a container in the tool that can be pressurized for delivery of the fluid tagged with the radionuclide tag. Depending on the environmental conditions downhole, the PET camera 202 and the computing unit (except the client interface/video interface) may be carried by the drillstring with the RSCT tool. Alternatively, only the PET camera 202 may be carried by the drillstring with the RSCT tool if the environmental conditions are not conducive to positioning the computing unit in the drillstring. Fluid mobility data can be transmitted to the client interface/video interface at the surface for analysis over a fast optical line, for example. After determining fluid mobility for the rock sample, it may be transferred to a storage tube.

Figure 3:
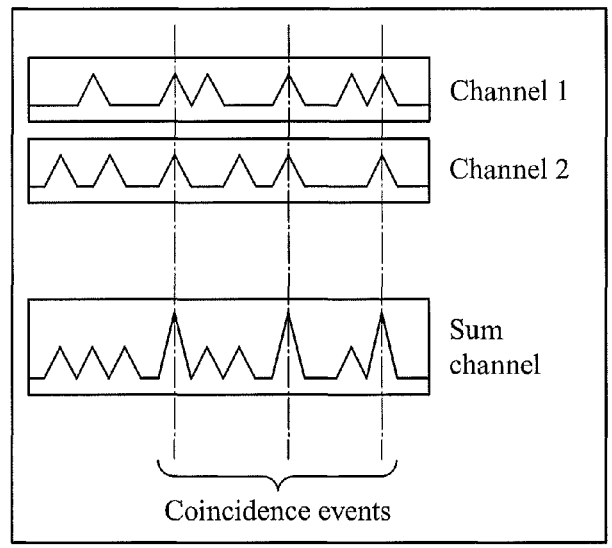
FIG. 3 illustrates coincidence event counting.
Figure 4:
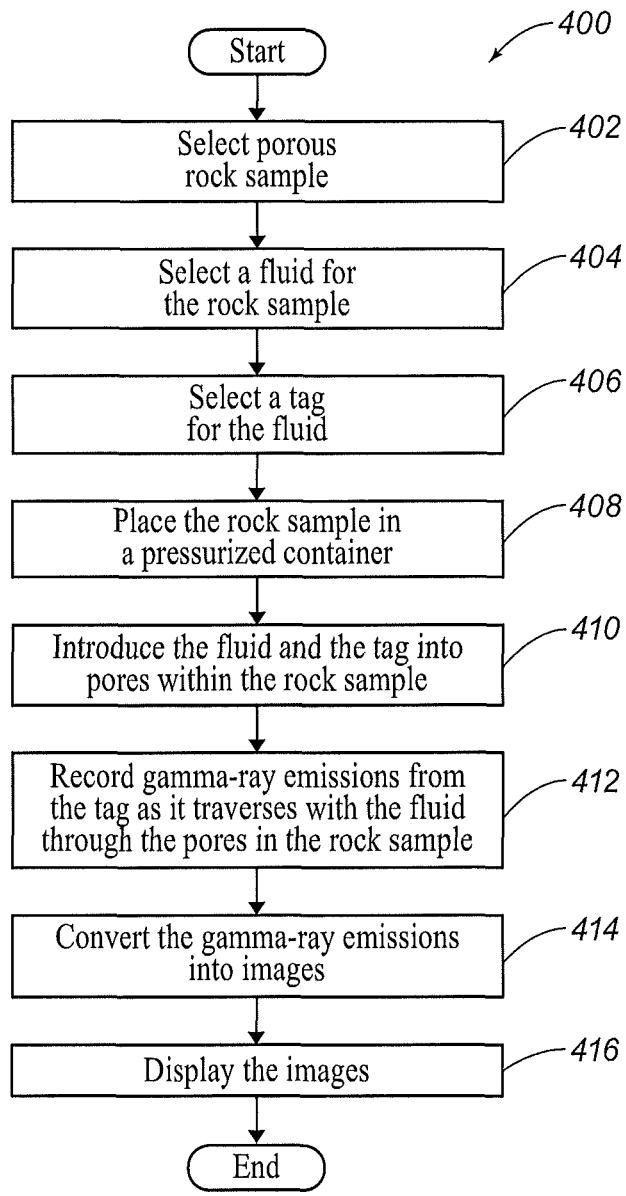
FIG. 4 if a flow diagram illustrating one embodiment of a method for implementing the present invention.

The memory primarily stores the application programs, which may also be described as program modules containing computer-executable instructions, executed by the computing unit for implementing the present invention described herein and illustrated in FIGS. 2-4. The memory therefore, includes a Data Acquisition Module and a Time-Lapse Data Analysis and Interpretation Module, which enable the methods illustrated and described in reference to FIG. 4.

The Data Acquisition Module records raw data (gamma ray emissions) in a list mode file. The gamma ray emissions are recorded as detected signals, which are recorded in chronological order so that each signal has a time stamp and the coordinates for each detector. When the signals significantly match or overlap for a pair of opposing detectors, a coincident event is defined. This mode of recording the raw data is further illustrated in FIG. 3 for recording coincidence events and is routinely utilized with a PET camera. Channels 1 and 2, for example, illustrate two independent signals representing a pair of opposing gamma ray emissions detected by a pair of opposing PET camera detectors at different times. The sum channel separates the coincidence events from other events (signals) by summing to determine a coincidence event within a predetermined short time interval. The Data Acquisition Module may therefore, be calibrated in a way to amplify the signal for only the time intervals where the amplitudes of the signals for channels 1 and 2 substantially overlap within a certain predefined short time interval. The coincidence event for the amplified signal amplitude therefore, may correspond to a pair of opposing gamma rays detected coincidentally within the predefined time interval. Each coincident event is recorded in chronological order so that each coincidence event has a time stamp and the coordinates for each of the two opposing detectors. Based on the coordinates for each of the two opposing detectors, the LOR may be easily determined. The Data Acquisition Module may record thousands of coincidence events per second. The list mode file therefore, secures the highest amount of available information for the raw data. Although case dependent, the size of the list mode file is much larger than that of a sinogram and can exceed hundreds of megabytes or even gigabytes of data. Once recorded, the data in the list mode file must be converted to form images that can then be used to determine fluid mobility.

The Time-lapse Data Analysis and Interpretation Module converts the data in the list mode file to images that can be used to determine fluid mobility. The conversion may be performed using conventional methods such as, for example, simple backprojection, filtered backprojection or iterative methods. The Time-Lapse Data Analysis and Interpretation Module uses a different method, however, to convert the list mode file to images. Each list mode file is segmented into time slices (typically of the order of a millisecond). The time-sliced data are triangulated to get the x,y,z,t coordinates for each tag, which enables tracking multiple tags in the field of view of the PET camera simultaneously. In this manner, tracking multiple tags may be extended to images and optimized for the size of the data matrices related to the number of image voxels. Any, well known and widely available image processing tool may be applied to optimize the quality of the image. Optionally, attenuation correction may be applied to improve the resolution of the processed voxel image by correcting for the so-called scattered and random coincidence, which contribute to the uncertainty of interpretation. Furthermore, uncertainty is associated with the speed of the moving tag. It seems that for slowly moving or stationary tags, the uncertainty is about half the detector size (i.e. about 2 mm). As the speed of the tag increases, this uncertainty increases proportionately and may require further investigation. Dealing with "non-continuous" data (i.e. fluid/gas propagation discretized into (ultra) short timeframes) may reduce this uncertainty, however.

Although the computing unit is shown as having a generalized memory, the computing unit typically includes a variety of computer readable media. By way of example, and not limitation, computer readable media may comprise computer storage media. The computing system memory may include computer storage media in the form of volatile and/or nonvolatile memory such as a read only memory (ROM) and random access memory (RAM). A basic input/output system (BIOS), containing the basic routines that help to transfer information between elements within the computing unit, such as during start-up, is typically stored in ROM. The RAM typically contains data and/or program modules that are immediately accessible to and/or presently being operated on by the processing unit. By way of example, and not limitation, the computing unit includes an operating system, application programs, other program modules, and program data.

The components shown in the memory may also be included in other removable/non-removable, volatile/non-volatile computer storage media or they may be implemented in the computing unit through application program interface ("API"), which may reside on a separate computing unit connected through a computer system or network. For example only, a hard disk drive may read from or write to non-removable, nonvolatile magnetic media, a magnetic disk drive may read from or write to a removable, non-volatile magnetic disk, and an optical disk drive may read from or write to a removable, nonvolatile optical disk such as a CD ROM or other optical media. Other removable/non-removable, volatile/non-volatile computer storage media that can be used in the exemplary operating environment may include, but are not limited to, magnetic tape cassettes, flash memory cards, digital versatile disks, digital video tape, solid state RAM, solid state ROM, and the like. The drives and their associated computer storage media discussed above provide storage of computer readable instructions, data structures, program modules and other data for the computing unit.

A client may enter commands and information into the computing unit through the client interface, which may be input devices such as a keyboard and pointing device, commonly referred to as a mouse, trackball or touch pad. Input devices may include a microphone, joystick, satellite dish, scanner, or the like. These and other input devices are often connected to the processing unit through a system bus, but may be connected by other interface and bus structures, such as a parallel port or a universal serial bus (USB).

A monitor or other type of display device may be connected to the system bus via an interface, such as a video interface. A graphical user interface ("GUI") may also be used with the video interface to receive instructions from the client interface and transmit instructions to the processing unit. In addition to the monitor, computers may also include other peripheral output devices such as speakers and printer, which may be connected through an output peripheral interface.

Although many other internal components of the computing unit are not shown, those of ordinary skill in the art will appreciate that such components and their interconnection are well known.

Method Description

Referring now to FIG. 4, a flow diagram illustrates one embodiment of a method 400 for implementing the present invention.

In step 402, a porous rock sample is selected. The rock sample may be selected based upon a number of criteria including, but not limited to, porosity characteristics and permeability. Shale, for example, may be selected as a porous rock sample with a permeability of less than one micro-darcy.

In step 404, a fluid for the rock sample is selected. The fluid may be selected, for example, based upon various criteria including, but not limited to, fluid indigenous to the rock sample. Thus, the fluid may be a gas or a liquid. If a shale rock sample is selected, then a fluid for the rock sample representing an indigenous fluid may be methane ($CH_4$) gas since methane is the main chemical constituent in shale gas.

In step 406, a tag for the fluid is selected. The radionuclide tag should resemble the fluid it is being used to tag for consistent results in determining fluid mobility. For example, a liquid should be tagged with a liquid radionuclide tag and a gas should be tagged with a gas radionuclide tag. For even better results, the radionuclide tag should have a chemical composition as close to the chemical composition of the fluid as possible. In this manner, the mobility of the fluid tag with the radionuclide tag will be closer to the true mobility of the fluid in the rock sample without the radionuclide tag. In turn, the activity of the radionuclide tag depends on both its size and composition. Thus, for shale, if a methane ($CH_4$) gas is selected as the fluid, a preferred radionuclide tag for the gas would be $C_{11}$.

In step 408, the rock sample is placed in a pressurized container. The pressurized container, for example, may resemble the pressurized container 206 described in reference to FIG. 2.

In step 410, the fluid and the tag are introduced into pores within the rock sample. The fluid and the tag may be introduced into the pores within the rock sample by injecting the fluid and the tag into the pressurized container at one end under a constant pressure and a constant temperature. Alternatively, the fluid and the tag may introduced into the pores within the rock sample by injecting the fluid and the tag directly into the pores within the rock sample before the rock sample is placed in the pressurized container and applying a constant pressure and a constant temperature to the rock sample after it is placed in the pressurized container with the fluid and the tag. The fluid is tagged when it is introduced with the tag into the pores within the rock sample. At this point, the tag attaches to the fluid as it traverses with the fluid through the pores within the rock sample and/or the tag travels with the fluid as it traverses with the fluid through the pores within the rock sample. Furthermore, multiple tags may introduced with the fluid into the pores within the rock sample. The fluid and the tag are introduced into the pores within the rock sample at a constant flow rate, a constant pressure and a constant temperature. The flow rate, the constant pressure, the constant temperature, the fluid and the tag may be selected based upon a flow rate, a pressure, and a temperature for a fluid that is indigenous to the rock sample, which represents a target fluid.

In step 412, gamma-ray emissions from the tag are recorded as the tag traverses with the fluid through the pores in the rock sample. Preferably, the gamma-ray emissions are recorded in a list mode file. The gamma-ray emissions may be recorded using the PET camera 202 and the Data Acquisition Module described in reference to FIG. 2.

In step 414, the gamma-ray emissions recorded in step 412 are converted into images. The gamma-ray emissions may be converted into images at a rate of more than one image every second using the Time-Lapse Data Analysis and Interpolation module described in reference to FIG. 2.

In step 416, the images form step 414 are displayed. The images may be displayed next to each other or consecutively using the client/video interface described in reference to FIG. 2. Fluid mobility may therefore, be determined by viewing the displayed images or using the displayed images to determine a permeability for the rock sample.

The proposed time-lapse PEPT technology therefore, greatly improves over state-of-the-art imaging technology because it actually images the fluid propagating through the rock sample under different net pressures. The time-lapse PEPT goes even further by performing un-compromised high-resolution imaging of fluid mobility and interactive scanning of rock samples with small-scale pores unprecedented in the rock physics industry.

Horizontal drilling and hydraulic fracturing have made it feasible to extract huge amounts of natural gas trapped in shale formations. The objective of fracturing techniques is to expose the maximum possible surface area of the rock formation and provide a reasonable path for the fluid to produce back to the wellbore. Fracturing techniques are therefore, designed to achieve long effective fracture half-lengths and improve fracture conductivity in rocks with mili-darcy (mD) to micro-darcy (μD) rock permeabilities. Fracturing techniques however, need to also address nano-darcy (nD) rock permeabilities in shale rocks that geologists used to consider seals. Permeability of a rock sample is defined as the ability of the rock sample to transmit fluids through the pore spaces, which influences the fluid flow rate, the fluid's movement and drainage of the fluid. The experimental determination of permeability in shale rock samples by standard rock physics laboratory measurements is extremely challenging and time-consuming. Therefore, rather than determining the bulk permeability for the shale rock sample, it is common practice to determine the Fracture Conductivity Ratio ($C_r$) by the following equation:

$$C_r = \frac{k_{fracture} \cdot w_{fracture}}{k_{reservoir} \cdot l_{fracture}} \quad (1)$$

where $k_{fracture}$ refers to fracture permeability (in mD), $w_{fracture}$ represents the width of the fracture (in ft), $k_{reservoir}$ is the formation/reservoir permeability (in mD) and $l_{fracture}$ represents the fracture half-length (in ft). It is common to refer to the product of $k_{fracture}$ and $w_{fracture}$ as the fracture conductivity (in mD ft).

The quantitative information on the fluid mobility, acquired with the time-lapse PEPT imaging will directly enhance the knowledge on $k_{reservoir}$, $w_{fracture}$ and $l_{fracture}$ parameters. As such, the time-lapse PEPT imaging will provide a unique quantitative estimate on how the fluid mobility changes as a result of fracturing, particularly at high fluid injection rates, where the conventional PET imaging fails. Furthermore, the time-lapse PEPT imaging will reduce the uncertainty in quantifying the Fracture Conductivity Ration ($C_r$) and moreover, the Natural Fracture Conductivity Index (NFCI) by direct one-to-one comparison of the fluid mobility of the pre-fracture rock sample with the post-fracture rock sample. This will provide for more accurate determination of fracturing production success, through the estimation of the Stimulated Reservoir Volume (SRV), defined as the product of the Stimulated Area and the Net Pay. The standard industrial practice for calculating SRV's usually introduces high uncertainty and systematic error in the volume estimates, mainly due to the inaccurate and uncertain estimates of the fracture connectivity. The three-dimensional PEPT fluid propagation imaging will produce a) more accurate estimates on the directionality of fractures deduced from the fluid distribution as a function of time, b) more quantitatively sound estimates of fracture connectivity and c) improved correlation and reduced error in the estimates of SRV.

Recent laboratory experiments performed on a number of shale rock samples reveal that the effective permeability of the shale rock sample can be changed from nD to μD when the shale rock sample is fractured. This suggests that even unsupported fractures (i.e. without the permeability support by proppant packs) may be capable of contributing to production in ultra-low permeability shale rocks. It is foreseen that by using the time-lapse PEPT imaging, it will be possible to derive quantitative (at least empirical) estimates on the correlation between the effective permeability of fractured rock, the estimates of SRV and the speed of fluid propagation front, directly from the reconstructed three-dimensional PEPT image. This will enable optimization and more time- and cost-efficient design of the fracturing and re-fracturing jobs by improving the knowledge on the correlation of fluid propagation and the fracturing attributes (e.g. closure stress), stimulation parameters (e.g. presence and type of proppants) and production data (e.g. pressure) as well as reduce uncertainty of the practical operational and economic variables, such as, for example: a) the amount of extractable hydrocarbons (e.g. Original Gas In Place), b) optimum well perforation interval, c) drainage area/volume of wells, d) recovery factor, e) optimum spacing units and f) optimum steer, direction and angle of the wells.

While the present invention has been described in connection with presently preferred embodiments, it will be understood by those skilled in the art that it is not intended to limit the invention to those embodiments. It is therefore, contemplated that various alternative embodiments and modifications may be made to the disclosed embodiments without departing from the spirit and scope of the invention defined by the appended claims and equivalents thereof.

The invention claimed is:

1. A method for determining fluid mobility in a rock sample using time-lapse positron emission particle tracking, which comprises the steps of:
   selecting a porous rock sample;
   selecting a fluid for the rock sample;
   selecting a tag for the fluid;
   placing the rock sample in a pressurized container;
   introducing the fluid and the tag into pores within the rock sample;
   recording gamma-ray emissions from the tag using a positron emission tomography camera as the tag traverses with the fluid through the pores in the rock sample placed in the pressurized container;

converting the gamma-ray emissions into images at a rate of more than one image every second; and
displaying the images.

2. The method of claim 1, wherein a permeability for the rock sample is less than one micro-darcy.

3. The method of claim 1, wherein the fluid for the rock sample is a gas and the tag for the fluid is the gas or another gas.

4. The method of claim 1, wherein the fluid for the rock sample is a liquid and the tag for the fluid is the liquid or another liquid.

5. The method of claim 3, wherein the fluid for the rock sample is $CH_4$ and the tag for the fluid is $C_{11}$.

6. The method of claim 1, wherein the gamma-ray emissions are recorded in a list mode file.

7. The method of claim 1, wherein the fluid and the tag are introduced into the pores within the rock sample by injecting the fluid and the tag into the pressurized container at one end under a constant pressure and a constant temperature.

8. The method of claim 1, wherein the fluid and the tag are introduced into the pores within the rock sample by injecting the fluid and the tag directly into the pores within the rock sample before the rock sample is placed in the pressurized container and applying a constant pressure and a constant temperature to the rock sample after it is placed in the pressurized container with the fluid and the tag.

9. The method of claim 1, wherein the fluid is tagged when it is introduced with the tag into the pores within the rock sample.

10. The method of claim 9, wherein the tag is attached to the fluid as the tag traverses with the fluid through the pores within the rock sample.

11. The method of claim 9, wherein the tag moves with the fluid as the tag traverses with the fluid through the pores within the rock sample.

12. The method of claim 1, further comprising introducing multiple tags with the fluid into the pores within the rock sample.

13. The method of claim 1, further comprising:
determining a permeability for the rock sample;
fracturing the rock sample;
determining a permeability for the fractured rock sample; and
comparing the permeability for the rock sample and the permeability for the fractured rock sample.

14. The method of claim 1, wherein the positron emission tomography camera is positioned in a drillstring.

15. The method of claim 1, wherein the fluid and the tag are introduced into the pores within the rock sample at a constant flow rate, a constant pressure and a constant temperature.

16. The method of claim 15, wherein the constant flow rate, the constant pressure, the constant temperature, the fluid and the tag are each selected based upon a target fluid.

17. The method of claim 16, wherein the target fluid represents a fluid within a rock formation from which the rock sample is taken or is likely to be found.

18. The method of claim 1, wherein the gamma ray emissions are emitted in pairs, each pair being emitted in almost opposite directions.

19. The method of claim 1, wherein the displayed images are displayed next to each other.

20. The method of claim 1, wherein the displayed images are consecutively displayed.

21. The method of claim 1, wherein fluid mobility is determined by viewing the displayed images or using the displayed images to determine a permeability for the rock sample.

22. The method of claim 5, wherein the rock sample is shale.

23. A method for determining fluid mobility in a rock sample using time lapse positron emission particle tracking, which comprises the steps of:
selecting a porous rock sample with a permeability less than one micro-darcy;
selecting a fluid for the rock sample that is a gas;
selecting a tag for the fluid that is the gas or another gas;
placing the rock sample in a pressurized container;
introducing the fluid and the tag into pores within the rock sample;
recording gamma-ray emissions from the tag in a list mode file using a positron emission tomography camera as the tag traverses with the fluid through the pores in the rock sample placed in the pressurized container;
converting the gamma-ray emissions into images; and
displaying the images.

24. The method of claim 23, wherein the gamma-ray emissions are converted into images at a rate of more than one image every second.

25. The method of claim 23, wherein the fluid for the rock sample is $CH_4$ and the tag for the fluid $C_{11}$.

26. The method of claim 23, wherein the fluid and the tag are introduced into the pores within the rock sample by injecting the fluid and the tag into the pressurized container at one end under a constant pressure and a constant temperature.

27. The method of claim 23, wherein the fluid and the tag are introduced in the pores within the rock sample by injecting the fluid and the tag directly into the pores within the rock sample before the rock sample is placed in the pressurized container and applying a constant pressure and a constant temperature to the rock sample after it is placed in the pressurized container with the fluid and the tag.

28. The method of claim 23, wherein the fluid is tagged when it is introduced with the tag into the pores within the rock sample.

29. The method of claim 25, wherein the rock sample is shale.

30. The method of claim 23, further comprising:
determining a permeability for the rock sample;
fracturing the rock sample;
determining a permeability for the fractured rock sample; and
comparing the permeability for the rock sample and the permeability for the fractured rock sample.

* * * * *